(12) United States Patent
Lopez

(10) Patent No.: US 6,177,078 B1
(45) Date of Patent: Jan. 23, 2001

(54) MONOCLONAL ANTIBODY ANTAGONISTS TO IL-3

(75) Inventor: Angel F Lopez, Adelaide (AU)

(73) Assignee: Medvet Science Pty Limited (AU)

( * ) Notice: Under 35 U.S.C. 154(b), the term of this patent shall be extended for 0 days.

(21) Appl. No.: 09/101,162

(22) PCT Filed: Dec. 24, 1996

(86) PCT No.: PCT/AU96/00840

§ 371 Date: Jun. 29, 1998

§ 102(e) Date: Jun. 29, 1998

(87) PCT Pub. No.: WO97/24373

PCT Pub. Date: Jul. 10, 1997

(30) Foreign Application Priority Data

Dec. 29, 1995 (AU) .................................................. PN 7368
Jan. 4, 1996 (AU) .................................................. PN 7418

(51) Int. Cl.[7] ........................ A61K 39/00; A61K 39/395; A61K 39/44; C07K 16/28

(52) U.S. Cl. .................................... 424/143.1; 424/130.1; 424/139.1; 424/141.1; 424/142.1; 424/143.1; 435/326; 435/334; 530/388.1; 530/388.22

(58) Field of Search .............................. 424/130.1, 131.1, 424/141.1, 142.1, 143.1; 435/326, 334; 530/388.22, 388.1

(56) References Cited

U.S. PATENT DOCUMENTS 5,747,032 * 5/1998 Metcalf et al. .................... 424/133.1

FOREIGN PATENT DOCUMENTS

WO 94/091-49  4/1994 (WO).

OTHER PUBLICATIONS

Sato et al, Blood vol. 82 No. 3, pp. 752–761, Aug. 1993.*
Callard and Gearing, Cytokine Facts Book, Academic Press, pp. 48–49 and 141–142, 1994.*
Devos, R et al. 1995. "Interleukin–5 and its receptor:a drug target for eosinophilia associated with chronic allergic disease," *Journal of Leukocyte Biology* 57:813–819.
Korpelainen, E.I. et al., 1995. "Interferon–γ upregulates Interleukin –3 (IL–3) Receptor expression in Human Endothelial Cells and synergizes with IL–3 in stimulating Major Histocompatibility Complex Class II Expression and Cytokine Production," *Blood* 86: 176–182.
Palacios, R. et al., 1986. "Monoclonal Antibodies Specific for Interleukin 3–Sensitive Murine Cells," *Journal of Experimental Medicine* 163:369–382.
Sun Q, et al., 1996. "Monoclonal Antibody 7G3 Recognizes the N–terminal domain of the Human Interleukin–3 (IL–3) Receptor α chain and functions as a specific IL–3 Receptor Antagonist," *Blood* 87:83–92.
Van der Hyden, J et al., 1991. "Characterization of the Murine IL–5 receptor complex with the use of a panel of monoclonal antibodies; relationship to the Murine IL–3 Receptor," *The Journal of Immunology* 147:3416–3417.

* cited by examiner

*Primary Examiner*—Prema Mertz
*Assistant Examiner*—Fozia Hamud
(74) *Attorney, Agent, or Firm*—Henry D. Coleman; R. Neil Sudol (57) ABSTRACT

Anti IL-3 Receptor alpha chain monoclonal antibody (MoAb) is the product of a hybridoma cell line designated 7G3. The MoAb acts as an antagonist to IL-3 in vitro activity. The MoAb binds to the N terminal domain of the IL-3 receptor alpha chain and does so competitively with IL-3 which indicates that this is, at least in part, involved in IL-3 binding. Treatment with the MoAb or fragment thereof, whether recombinant or otherwise, may be suitable for the treatment of one or more of the following conditions: myeloid leukemias, lymphomas such as follicular B cell lymphoma, or the alleviation of allergies.

10 Claims, 8 Drawing Sheets

MONOCLONAL ANTIBODY ANTAGONISTS TO IL-3

RELATED APPLICATIONS

This application is a §371 filing of PCT/AU96/00840 (WO 97/24373), filed Dec. 24, 1996.

FIELD OF THE INVENTION

The present invention relates to monoclonal antibodies (MoAb) and reagents derived therefrom which are reactive with Haemopoietic Growth Factors, and especially with human interleukin 3 (IL-3) receptor α-chain and function as an antagonist to the Haemopoietic Growth Factors.

BACKGROUND OF THE INVENTION

Human interleukin-3 is a pleiotropic cytokine that stimulates the production of hemopoietic cells from multiple lineages including neutrophils, eosinophils, monocytes, megakaryocytes, erythroid cells, basophils and B cells. Recently IL-3 has also been shown to regulate vascular endothelial cell functions; enhancing adhesion molecule expression, neutrophil transmigration and cytokine production. Although some of the effects of IL-3 may be desirable and have prompted its clinical use in bone marrow reconstitution following chemotherapy, it is also apparent that abnormal or excessive production of IL-3 has the potential to lead to disease states. For example, some acute myeloid leukaemias proliferate in response to IL-3, and cells from follicular B cell lymphomas produce and depend on IL-3 for their growth. IL-3 has also been implicated in allergy not only for its ability to stimulate eosinophil and basophil production but also for being a strong stimulus of histamine release from basophils in vitro. The detection of elevated amounts of IL-3 mRNA in the skin and bronchi of allergic individuals further suggests an in vivo role in allergy.

The biological activities of human IL-3 are initiated by the binding of IL-3 to its receptor. This consists of two subunits; an α chain (IL-3Rα) which binds IL-3 specifically and with low affinity,[16] and a β chain ($β_c$) which does not bind ligand on its own but confers high affinity binding when co-expressed with IL-3Rα.[17,18] Both chains are required for signalling,[18] however, receptor activation and cellular signalling are dependent on IL-3 binding to IL-3Rα as the initial step. The subsequent events are not fully understood but probably involve receptor dimerization leading to the activation of specific kinases associated with the receptor.[19,43]

The structure of the extracellular domain of human IL-3Rα has not yet been elucidated. Since IL-3Rα belongs to the cytokine receptor family, it is predicted to contain a cytokine receptor module (CRM) with two discrete folding domains.[20] In addition there is also an N-terminal domain which, interestingly, has sequence similarities with the human GM-CSF and IL-5 receptor α chains.[21] This feature distinguishes these receptors from the other members of the cytokine receptor family. The functions of the CRM and N-terminal domain of the IL-3Rα chain are not known, nor is it known where the IL-3 binding regions lie in the receptor.

SUMMARY OF THE INVENTION

The present invention arises in part as a result of the preparation and the characterization of a monoclonal antibody, MoAb 7G3, directed against the IL-3Rα chain which is capable of inhibiting IL-3 binding, IL-3 receptor dimerization[43] and of antagonizing IL-3 functions. These results offer the potential to block IL-3 activity in vivo. A single MoAb to hIL-3R α-chain has been previously described[35], which recognizes subpopulations of peripheral blood and bone marrow cells. However this antibody does not act as an antagonist to IL-3.

Figure 4A:
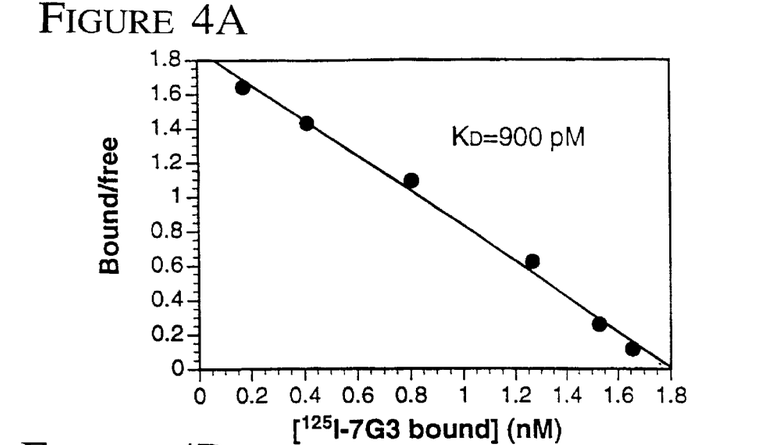
FIG. 4A is a Scatchard transformation of a saturation binding curve using $^{125}$I7G3 on F6 cells stably expressing the IL-3R α chain.
Figure 5A:
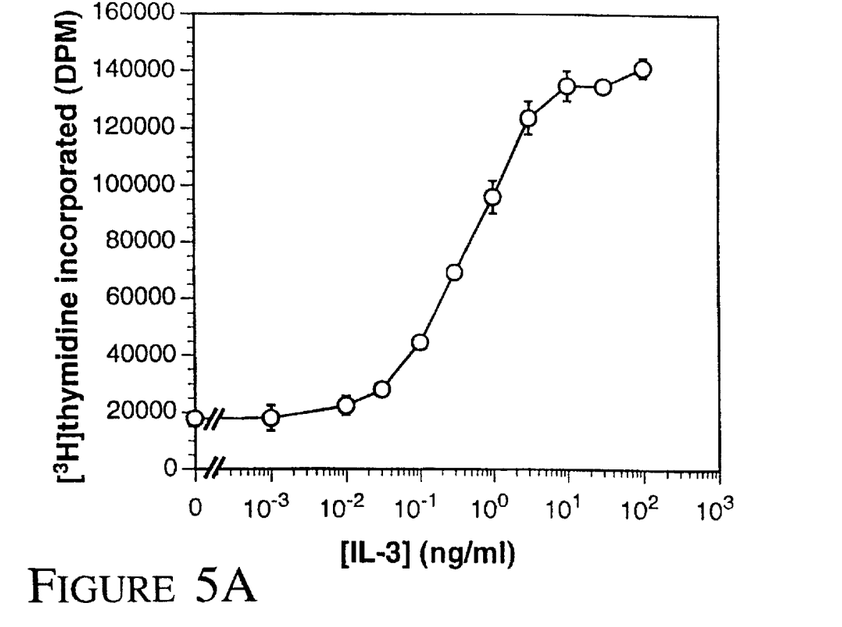
FIG. 5A is a plot showing TF-1 cell proliferation in response to different concentrations of IL-3.
Figure 5B:
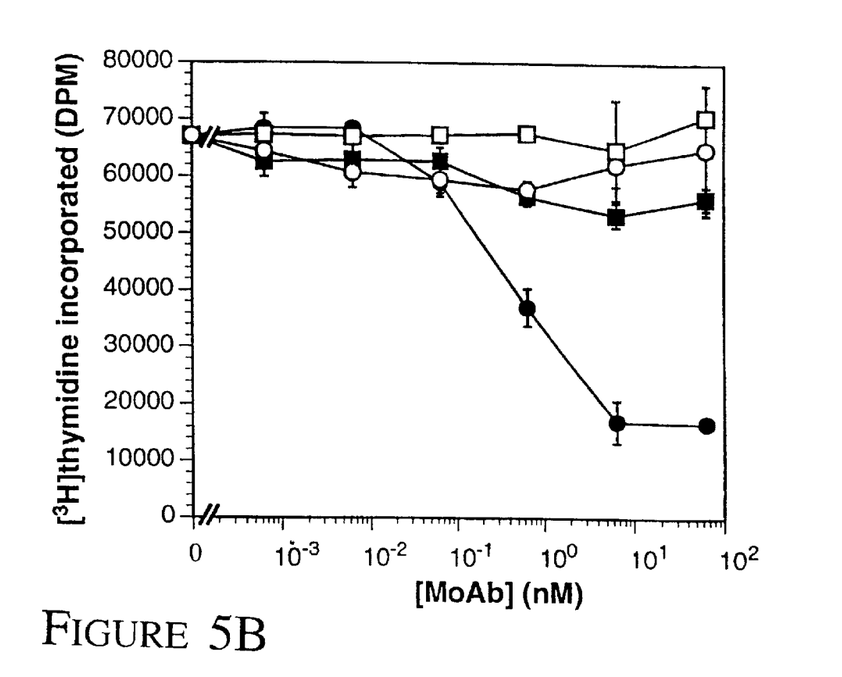
FIG. 5B is a plot showing TF-1 cell proliferation stimulated by 0.3 ng/ml of IL-3 in the presence of a range of concentrations of MoAb 7G3 (●), 6H6 (□), 9F5 (■) and a control MoAb (○).
Figure 6A:
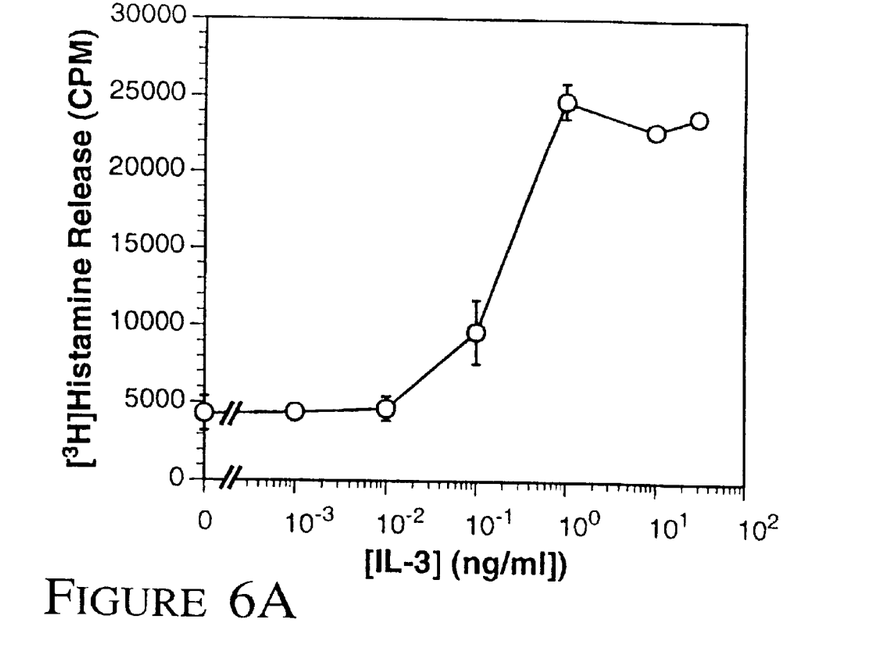
FIG. 6A Is a plot showing histamine release from human basophils in response to a range of concentrations of IL-3 and FIG. 6B Is a plot showing histamine release stimulated by 1 ng/ml of IL-3 in the presence of a range of concentrations of MoAb 7G3 (●), 9F5 (■) and the control MoAb (○).
Figure 6B:
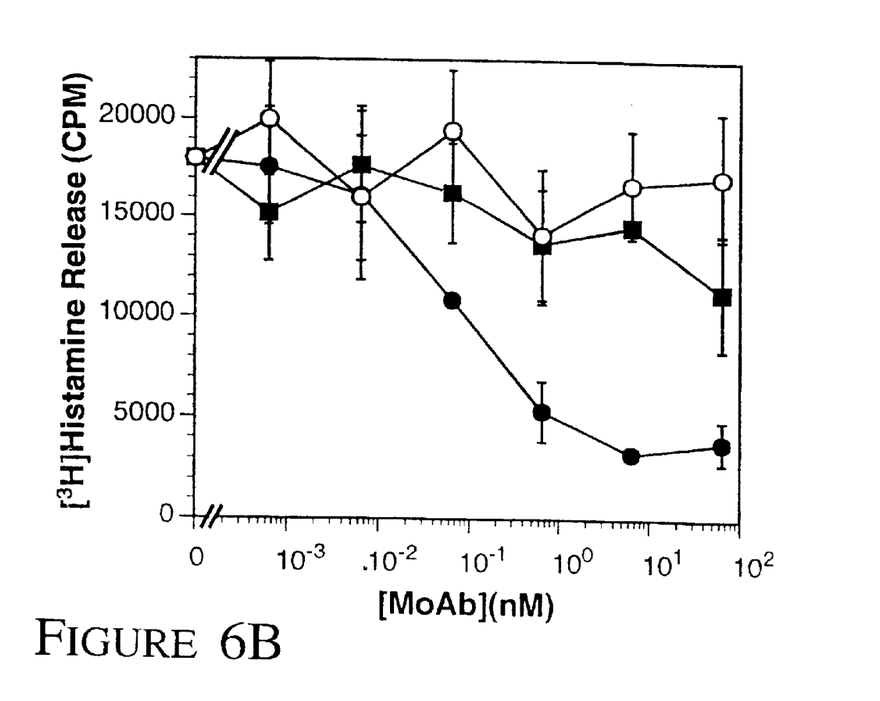
Figure 7A:
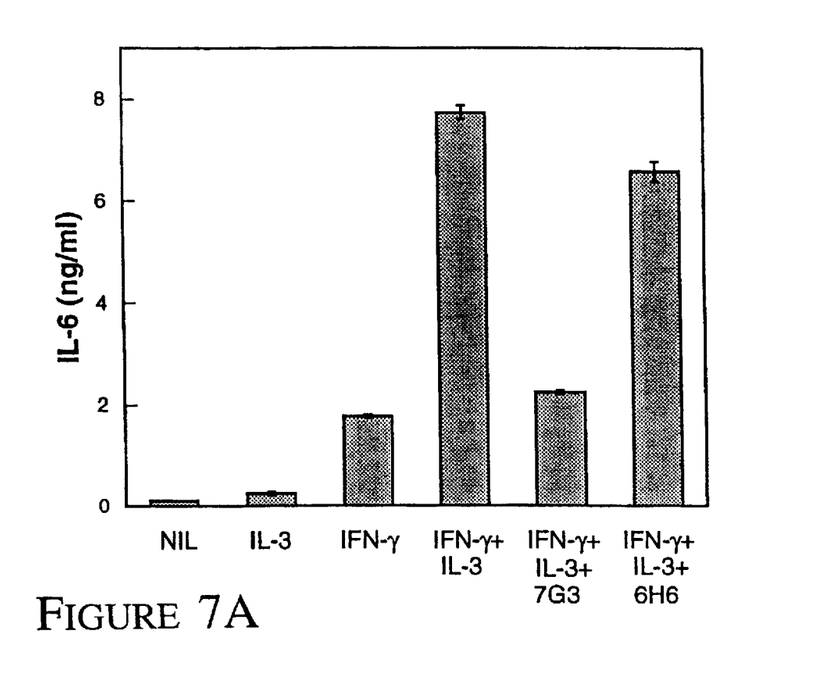
FIG. 7A. Is a representation showing that MoAb 7G3 selectively inhibits IL-3-mediated stimulation of IL-6 release from HUVEC stimulated by IL-3 (30 ng/ml) together with IPN-γ (100 U/ml) or TNF-α (100 U/ml).
Figure 7B:
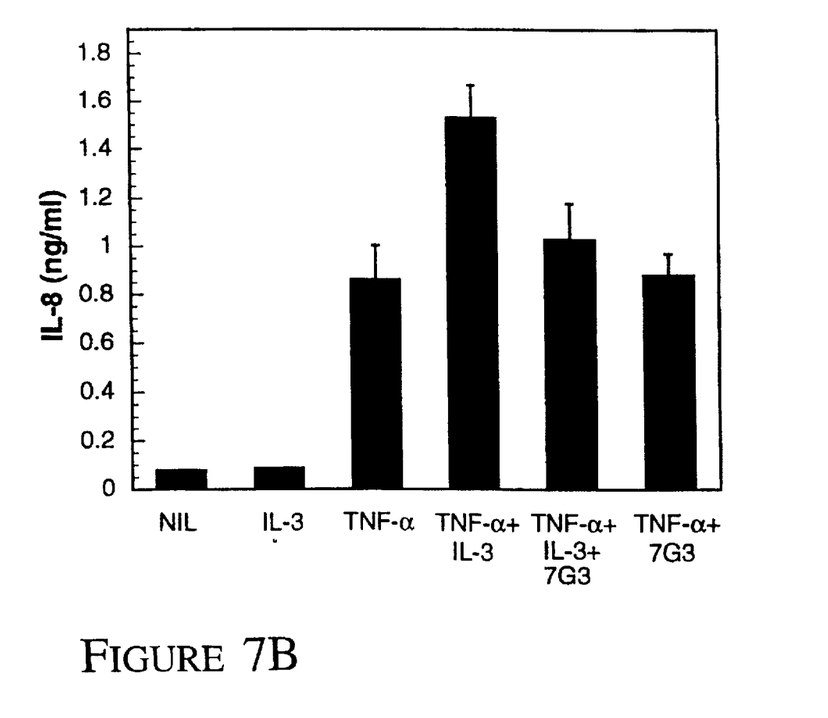
FIG. 7B Is a representation showing that MoAb 7G3 selectively inhibits IL-3-mediated stimulation of IL-8 release from HUVEC stimulated by IL-3 (30 ng/ml) together with IFN-γ (100 U/ml) or TNF-α (100 U/ml).

IL-3 is believed to play important roles in both haemopoiesis and inflammation. Although IL-3 has been shown to stimulate several cell types in vitro[37] it is somewhat puzzling that this cytokine has not been detected in the bone marrow or serum of normal animals;[38] suggesting that it is not required for basal haemopoiesis. On the other hand, the injection of IL-3 to mice and humans stimulate haemopoiesis as well as significant side-effects such as bone marrow fibrosis.[39,40] In this respect IL-3 may be viewed as a "reactive" rather than a "steady-state" cytokine and its production may lead to desirable as well as potentially deleterious effects. Consistent with this role, the production of IL-3 is under tight regulatory control in T cells.[41] We show here that MoAb 7G3 is an effective antagonist of IL-3 activities with an $ED_{50}$ of 0.4 to 1 nM, consistent with the its $K_D$ value (FIG. 4A). Three types of IL-3 functions were studied as the antagonism of IL-3 in these situations is likely to be of clinical significance. Firstly, MoAb 7G3 antagonized IL-3-mediated enhancement of histamine release from basophils (FIG. 6). Antagonizing IL-3 may be useful in allergic situations as elevated IL-3 mRNA has been noted in the skin and bronchi of atopic individuals,[15] and the presence of IL-3 may lead to excessive stimulation of basophils and eosinophils at allergic reaction sites. Secondly, the IL-3 mediated proliferation of the leukaemic cell line TF-1 was completely antagonized by MoAb 7G3 (FIG. 5) at similar concentrations to those described above. Antagonism of IL-3-mediated cell proliferation is likely to be useful in some leukaemias where IL-3 has been shown to promote growth.[10,11] In particular follicular B cell lymphomas which bind IL-3 with high affinity and proliferate in an IL-3 dependent manner[12] may be ideally suited for intervention with MoAb 7G3. Lastly, we found that MoAb 7G3 antagonized IL-3-mediated functions on HUVEC, namely the enhancement of TNF-α stimulation and the synergism with interferon γ (FIG. 7). The presence of IL-3 receptors on HUVEC and their upregulation by TNF-α and interferon γ has recently been noted,[7,8,34] and their stimulation by IL-3 enhances IL-8 and IL-6 production, HLA class II expression,[8] and neutrophil transmigration.[7] Although the full significance of these in vitro findings need to be ascertained, these effects are likely to contribute to a systemic phase of inflammation and may be amenable to control with MoAb 7G3.

In competition experiments we found that MoAb 7G3 and IL-3 reciprocally inhibited each others binding. This suggests that the IL-3 binding site may lie within or adjacent to the epitope recognized by MoAb 7G3.

Figure 8A:
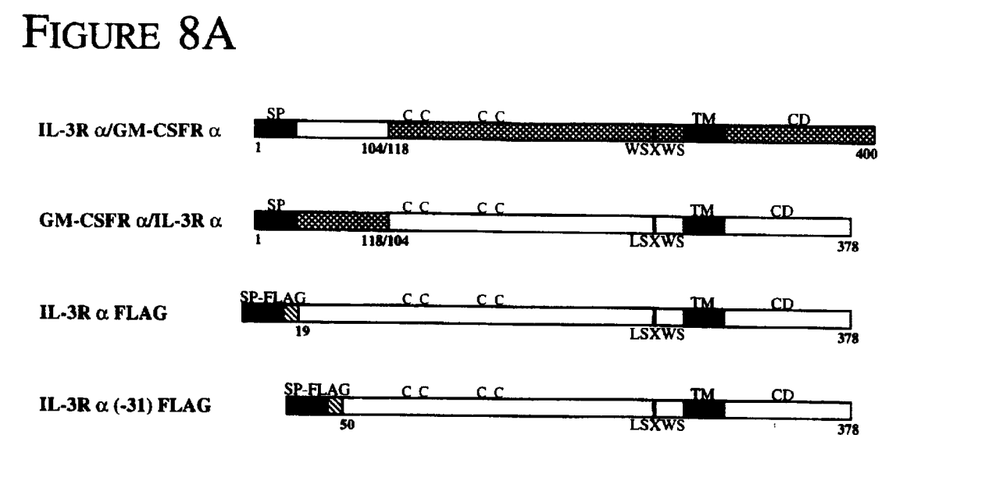
Figure 8B:
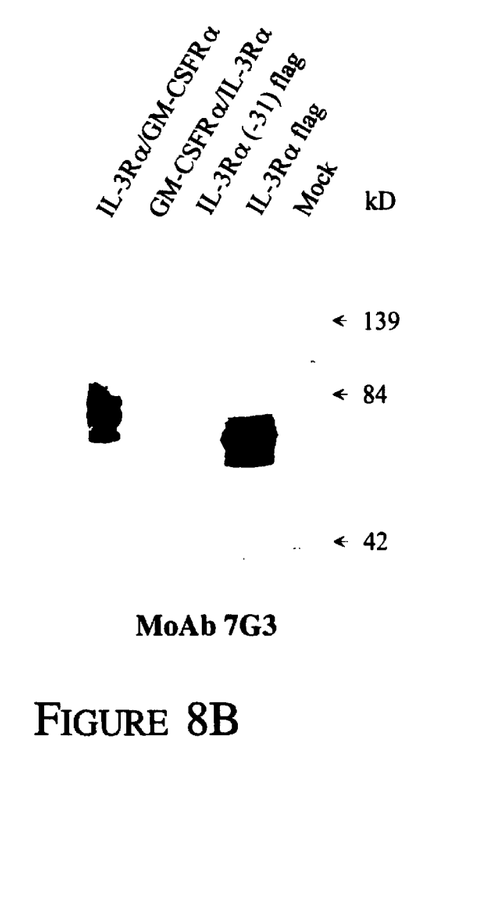
FIG. 8B Is a representation of the results of a Western blot analysis of COS cells transiently transfected with various IL-3Rα mutants. Binding of 7G3 was seen with the IL-3Rα/GM-CSFRα chimera (B, lane 1) and with the wild-type IL-3Rα containing a "flag" sequence interposed between the signal peptide and residue 19 (IL-3Rα flag) (B, lane 4) but not with the GM-CSFRα/IL-3Rα chimera (B, lane 2) nor with a truncated IL-3Rα lacking Thr$^{19}$-Asp$^{49}$ [IL-3Rα (−31) flag] (B, lane 3).
Figure 8C:
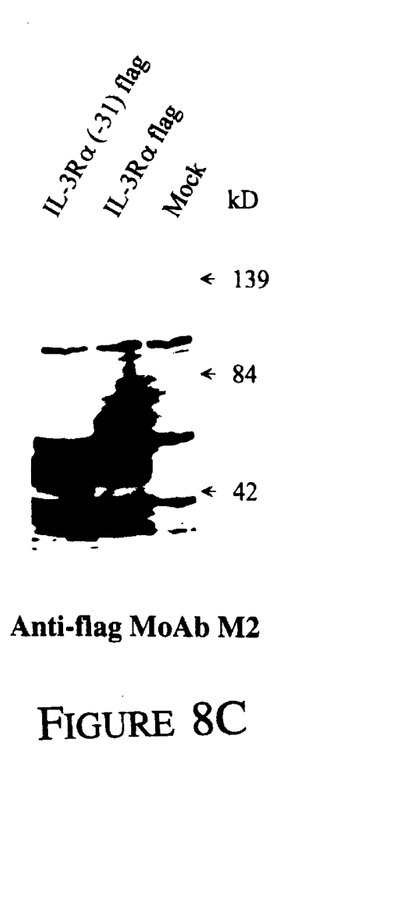
FIG. 8C Expression of IL-3Rα (−31) flag (C, lane 1) and IL-3Rα flag (C, lane 2) are demonstrated by Western Blot using an anti-flag MoAb M2.

We identified the N-terminal domain of IL-3Rα as a region required for MoAb 7G3 binding based on the positive immunofluorescence and Western blotting results with a chimeric receptor comprising the N-terminal domain of IL-3Rα and the CRM[21] of GM-CSFRα. In contrast, MoAb 7G3 failed to bind to a chimeric receptor comprising the N-terminal domain of GM-CSFRα and the CRM of the extracellular region of IL-3Rα (FIG. 8 and 9). This suggests that the N-terminal domain of IL-3Rα is necessary for MoAb 7G3 binding. Further truncations in the N-terminus with retention of MoAb 7G3 reactivity suggest that the 19–49 region of the N-terminal domain of IL-3Rα forms part of the epitope recognized by MoAb 7G3. In other experiments we have found that truncation of the N-terminal domain of IL-3Rα does not abolish the binding of IL-3 although the affinity of this binding is much decreased. These results have implications for defining the binding site for IL-3 and suggest that this may be formed by two non-contiguous regions in the primary structure of IL-3Rα, one of which is in the N-terminal domain and is recognized by MoAb 7G3. The existence of a conformational epitope for IL-3 and MoAb 7G3 is further supported by the inability of MoAb 7G3 to bind linear sequences as represented by the overlapping 14-amino acid peptides.

These results offer the potential to block IL-3 activity in vivo and suggest that the N-terminal domain of IL-3Rα, may be involved in ligand binding. An analogy may be drawn to suggest that the N-terminal domain of GM-CSFR and IL-5Rα chains, may also be involved in ligand binding because this domain is conserved amongst the IL3Rα, GM-CSFRα and IL-5Rα family.[21]

In one broad form the invention might be said to reside in a monoclonal antibody or antibody fragment with a binding specificity to the N-terminal domain of the IL-3 receptor α chain, or of a homologous region of another haemopoietic receptor said antibody or antibody fragment capable of antagonising functions of the IL-3 or of the haemopoietic receptor respectively.

In an alternative broad form the invention could be said to reside in a monoclonal antibody or antibody fragment or any other compound, peptide or oligonucleotide, with a binding specificity to amino acid residues 19–49 of the IL-3 receptor a chain, or of a homologous region of another haemopoietic receptor.

The other haemopoietic receptor may be selected from the group of receptors responsible for binding GM-CSF, IL-2, IL-3, IL-4, IL-5, IL-6, IL-7, IL-9, IL-10, IL-11, IL-13, IL-14, IL-15 and others of this family yet to be discovered, granulocyte colony stimulating factor (G-CSF), erythropoietin (EPO) and thrombopoietin (TPO), the monoclonal antibody or antibody fragment being an antagonist of the respective Haemopoietic growth factor.

In an alternative form the invention could be said to reside in a monoclonal antibody or antibody fragment being an antagonist to any one or more of the group comprising IL-3, GM-CSF and IL-5, and preferably IL-3.

As a further alternative the invention could be said to reside in a monoclonal antibody or antibody fragment being an antagonist to IL-3 activity Alternatively the invention could be said to reside in a monoclonal antibodies or a fragment thereof produced by the 7G3 hybridoma cell line.

It is to be understood that where reference is made to a fragment of a monoclonal antibody the term to include but not be limited to Fab, Fv and peptide fragments of the monoclonal antibody, it may also include such fragments when made as part of a different larger peptide or protein, which may be the product of a recombinant vector. Thus the variable region of the respective monoclonal antibody may be cloned and be made part of a hybrid protein with properties appropriate for the therapeutic purposes of the respective agent.

The invention may also be said to reside in the method of making a monoclonal antibody, said monoclonal antibody being active as an antagonist to a haemopoietic growth factor, said method including the step of immunizing an animal with a fragment of a haemopoietic growth factor receptor fragment including N-terminal domain of IL-3 α chain or of another haemopoietic growth factors, isolating antibody producing cells from the immunised animal and fusing said antibody producing cell with a myeloma cell to produce a pool of hybridoma cells, and screening the pool of hybridoma cells for cells that produce the monoclonal antibody.

Whilst monoclonal antibodies may be successfully used therapeutically, they are large proteins that have to be administered parenterally. Additionally they may evoke an immune response in the recipient and it is to be understood that monoclonal antibody fragments are preferably used instead of whole antibodies.

The invention therefore may reside in a therapeutic agent including a Fab, Fv or peptide fragment of a monoclonal antibody directed at amino acids 19–49 of the N-terminal domain of IL-3Rα chain, or of a homologous region of another haemopoietic growth factor receptor, said therapeutic agent acting as an antagonist to the respective haemopoeitic growth factor.

It is postulated that binding of other compounds to the same region as monoclonal antibody 7G3 or homologous regions are likely to have a similar effect. Such compounds may include peptides, oligonucleotides, amino acids, nucleic acids, or sugars. Such compounds could be isolated by screening for binding to amino acids 19–49. Accordingly the invention may be said to reside in a therapeutically active compound with a binding specificity for the N-terminal domain of IL-3Rα chain and perhaps to the amino acids 19–49 of the N-terminal domain of IL-3Rα chain, or of a homologous region of another haemopoeitic growth factor receptor, said therapeutic agent acting as an antagonist to the respective haemopoeitic growth factor.

For example, a scramble of randomly synthesised oligonucleotides could be passed through a solid matrix in which a peptide of part or all of amino acids 19–49 of the N-terminal domain of IL-3Rα chain, or of a homologous region of another haemopoietic growth factor receptor. Following washing the strongly binding oligonucleotides remain and can then be eluted under different conditions (salt, ph etc). The sequence can then be determined by PCR and tested for inhibition of IL-3 on a real cell system.

The invention may also reside in a pharmaceutical preparation including the therapeutic agent, antibody, or antibody fragment defined above, in a pharmaceutically effective carrier. Such a preparation may be administered parenterally in dosage forms or formulations containing conventional nontoxic pharmaceutically acceptable carriers. Alternatively, and preferably, the agents are small enough so that they can be absorbed via the gut, so that they may be taken orally. The formulation and preparation of any of these pharmaceutical compositions using antibodies, antibody fragments which may or may not be composed of hybrid proteins is well known to those skilled in the art of pharmaceutical formulation. Specific formulation can, however, be found in the text entitled "Remington's Pharmaceutical Sciences", Sixteenth Edition, Mack Publishing company, 1980.

It will be understood from that an antagonist of IL-3 may be useful in the treatment of leukaemias such as myeloid leukaemias, lymphomas such as follicular B cell lymphomas, or the alleviation of allergies, the invention might also be said to comprise a method of treatment or prevention of such conditions by administering a therapeutically effective dose of a therapeutic agent, or antibody, or antibody fragment as defined above in a pharmaceutically acceptable carrier.

BRIEF DESCRIPTION OF THE DRAWINGS

In FIG. 2A $^{124}$I-IL-3 was used at 4 nM and in FIG. 2B at 150 pM. In both FIGS. 2A and 2B The dashed line represents competition by 200 fold excess unlabelled IL-3 and each point is the mean of triplicate determinations and the error bars represent standard deviations.

In FIGS. 5A and 5B each point represents the mean of triplicate determinations and the error bars represent standard deviations.

In FIGS. 6A and 6B each value represents the mean of quadruplicate determinations and the error bars represent standard deviations.

In FIGS. 7A and 7B MoAb 7G3 was used at 30 µg/ml and the values represent the means of triplicate determinations and the error bars represent standard deviations.

FIG. 8A. Is a schematic representation of the IL-3Rα constructs used to epitope map MoAb 7G3. SP=signal peptide; TM=transmembrane region; CD=cytoplasmic domain. The conserved cysteines (c) and WSXWS motifs are indicated. The numbering of the primary sequence includes the signal peptide. The shaded regions represent GM-CSFRα chain and the clear regions IL-3Rα chain encoding DNA.

EXAMPLES

Materials and Methods

Cell lines, media and cytokines. The CHO (Chinese Hamster Ovary) cell line F6, expressing the IL-3Rα chain was developed for screening and characterization of anti-IL-3Rα MoAbs. Briefly, IL-3R α-chain cDNA was cloned into pcDNA1Neo (Invitrogen, San Diego, Calif.) and transfected into CHO cells by electroporation.[22] COS (Monkey Fibroblast) cells transiently transfected with IL-3R α-chain cDNA by electroporation[23] with or without βc cDNA were used for immunization and characterization of anti-IL-3Rα chain MoAb. TF-1 cells were maintained in RPMI supplemented with 10% FCS and GM-CSF (2 ng/ml). GM-CSF was a gift from Genetics Institute (Cambridge, Mass.). Recombinant human IL-3 was produced in *E. coli* as previously described.[24]

Generation of MoAbs. BALB/c mice were immunized intraperitoneally with 5×10$^6$ COS cells transfected with the IL-3Rα chain in combination with 100 µg of Adjuvant Peptides (Sigma). This procedure was repeated three times at two week intervals. Four weeks after the final immunization, a mouse was boosted intravenously with 2×10$^6$ COS cell transfectants. Three days later the splenocytes were fused with the mouse NS-1 myeloma cells at the ratio of 4:1 using 50% polyethylene glycol as described.[25] After fusion the cell suspension was cultured in RPMI-1640 supplemented with 20% FCS and 20% J774 conditioned medium.[26] Hybridoma cells were selected with hypoxanthine-aminopterin-thymidine (HAT). Hybridoma supernatants were screened using F-6 cells by an antigen capture immunoassay with Rose Bengal as a calorimetric indicator.[27] Positive clones were subcloned by limiting dilution and the culture conditions were gradually reduced to RPMI-1640 complete media supplemented with 10% FCS. Antibody-containing ascites fluid was produced by injecting the hybridoma cells into pristane-treated mice. MoAbs were purified from the ascites on a protein A Sepharose Column (Pierce, Rockford, Ill.) as described by the manufacturer. The MoAbs were isotyped by means of a mouse-hybridoma subtyping kit (Boehringer Mannheim, Mannheim, Germany).

Immunofluorescence. Freshly purified neutrophils, eosinophils, monocytes, human umbilical cord venular endothelial cells (HUVEC) or F6 cells (5×10$^5$) were incubated with 50 μl of hybridoma supernatant or 0.25 μg of purified MoAb for 45–60 min at 4° C. Cells were washed twice and then incubated with FITC-conjugated rabbit anti-mouse Ig (Silenus, Hawthorn, Victoria, Australia) for another 30–45 min. The fluorescence intensity was analysed on an EPICS-Profile II Flow Cytometer (Coulter Electronics). In experiments with truncated IL-3Rα chain and IL-3Rα/GM-CSFRα chimera, the transfected COS cells were examined under a fluorescence microscope.

Immunoprecipitations. F6 cells (4×10$^7$) were surface labelled using Na $^{125}$I (New England Nuclear, Boston, Mass.) as described.[21] Cells were washed three times with PBS and lysed in 1 ml of RIPA buffer with protease inhibitors [25 mM Tris-HCl, pH 7.4, 150 mM NaCl, 1% Triton, 0.5% Deoxycholate, 0.05% SDS, 2 mM PMSF, 10 mM Soybean Trypsin Inhibitor, 20 mM Leupeptin and 5% Aprotonin (Sigma, St Louis, Mo.)]. The cell extracts were centrifuged at 10,000 g for 15 min and the cell lysates were precleared twice with protein A sepharose before incubating 250 μl of lysates with MoAbs (2 μg/ml) overnight at 4° C. Protein-A Sepharose was then added and bound proteins were washed with RIPA buffer and eluted with SDS loading buffer with 2-mercaptoethanol and analysed by 10% SDS-PAGE. Radiolabelled proteins were visualized using an ImageQuant PhosphorImager (Molecular Dynamics, Sunnyvale, Calif.).

Western blotting. F6 cells (3×10$^7$) were solubilized in reducing SDS loading buffer, and the proteins separated by 10% SDS-PAGE before transferring electrophoretically onto nitrocellulose filters. Filters were then blocked with TNT buffer (10 mM Tris-Cl pH 8.0, 150 mM NaCl, 0.05% Tween-20) containing 3% gelatin. The anti-IL-3Rα MoAbs (2 μg/ml) were diluted in TNT buffer containing 1% gelatin and incubated with the filters for 90 min. The filters were then incubated with $^{125}$I-Protein A (New England Nuclear, Boston, Mass.) for 45 min and washed thoroughly with TNT buffer. The radio-labelled proteins were detected as described above. For Western blot analysis of truncated and chimeric IL-3Rα chains, gels were electroeluted onto PVDF membrane and filters blocked in 5% BSA in Tris-buffered saline with 0.05% Tween-20 (TTBS). Filters were incubated with MoAbs (1–10 μg/ml) in TTBS with 5% BSA for 2 hours. Flag tagged proteins were detected with 3 μg/ml anti-flag MoAb M2 (IBI, New Haven, Conn.). The secondary antibody, alkaline phosphatase tagged goat anti-mouse (Pierce, Rockford, Ill.) was then added at a dilution of 1:2500 in TTBS. The MoAb bound proteins were visualized using the BCIP/NBT Western Blue stabilized substrate (Promega) as described by the manufacturer.

Radioiodination of IL-3 and binding assays. Radioiodination of IL-3 and binding assays were performed as previously described.[29] Briefly, low affinity binding assays were carried out by incubating 4 nM of $^{125}$I-IL-3 with 5×10$^5$ F6 cells at room temperature for 2½ hours in RPMI medium containing 0.5% BSA and 0.1% Sodium Azide. After centrifuging through FCS, radioactivity in the cell pellet was determined by a Packard Auto-Gamma 5650 (Meriden, Conn.). When high affinity binding assays were performed 150 pM of $^{125}$I-IL-3 and 7×10$^5$ COS cells co-expressing IL-3R α and chains were used. In competition experiments, cells were incubated with $^{125}$I-IL-3 in the presence of a range of concentrations of MoAb 7G3 or IL-3.

Radioiodination of MoAb 7G3 and binding assays. 10 kg of MoAb 7G3 was iodinated with 0.5 mCi of Na$^{125}$I by the Chloramine T method as described.[30] Saturation binding studies were performed by incubating 5×10$^5$ F6 cells with $^{125}$I-7G3 over a range of concentrations (0.0018 nM–20 nM) in the presence or absence of 100 fold excess of unlabelled MoAb 7G3. The binding curve was analysed by Scatchard transformation.[31] In competition binding experiments F6 cells or COS cells co-expressing IL-3R α and β chains were preincubated for 2 hours at 4° C. with a range of concentrations of IL-3 or GM-CSF before adding 1 nM of $^{125}$I-7G3 for a further 2 hours.

Inhibition of IL-3-mediated TF-1 cell proliferation assay. TF-1 cells were starved of GM-CSF for 24 to 48 hours before setting up proliferation assays. Briefly, 1×10$^4$ cells were incubated in wells with 0.3 ng/ml of IL-3 in the presence of a range of concentrations of MoAbs (0.00064–64 nM) for 48 hours at 37° C. Wells were pulsed with 0.5 μCi/well $^3$H-thymidine for 4 hours and then harvested onto a glass filter and radioactivities determined by liquid scintillation. The results were expressed as disintegrations per minute (DPM).

IL-3-mediated histamine release from human basophils. Histamine release assay was determined as previously described.[14] Briefly, low density leukocytes were separated from peripheral blood by dextran sedimentation and centrifugation on Lymphoprep (Nycomed, Oslo, Norway). Cell suspension (containing 1–2% of basophils) were preincubated with purified human IgE for 45 min before incubating 1×10$^6$ cells with IL-3, a goat IgG anti-human IgE (0.8 μg/ml) and a range of concentrations (0.00064–64 nM) of MoAbs for a further 60 min. The released histamine was quantified subsequently using a radioenzymatic method.[32]

IL-3-mediated functions on endothelial cells. The effect of MoAbs on the IL-3 stimulated secretions of IL-6 and IL-8 by HUVEC was studied. HUVEC were obtained and cultured as previously described.[33] For IL-6 measurements, HUVEC (5×10$^5$ per well) were treated with IFN-γ (100 U/ml) for 48 hours, IL-3 (30 ng/ml) for 24 hours, or IFN-γ for 48 hours with IL-3 added for the last 24 hours with or without MoAbs 7G3 or 6H6 (100 μg/ml). After treatment the medium was changed and supernatants were collected for 24 hours and analysed for the presence of immunoreactive IL-6 using an ELISA method (Quantikine, R & D Systems, Minneapolis, Minn.). IL-8 production was measured as previously described.[7] Briefly, HUVEC (5×10$^5$ per well) were incubated with TNF-α (100 U/ml) for 24 hours and or, IL-3 (30 ng/ml) for 6 hours, with or without MoAb 7G3 (50 μg/ml). After incubation the medium was changed and the IL-8 secreted in the following hour was quantified by ELISA.

Construction and expression of chimeric and truncated IL-3Rα chains. IL-3Rα/GM-CSFRα chimera: this fusion cDNA encodes a chimeric receptor composed of the first 104 amino acids of IL-3Rα including the signal sequence fused to amino acids 118–400 of the GM-CSFRα-chain. It was generated by PCR using a sense primer 5' to the IL-3Rα coding sequence and an antisense primer corresponding to codons 104–99 and including a Kpn 1 site. The sequence of the resulting PCR product was checked and it was then ligated in-frame to the Kpn 1 site at codon 118 of GM-CSFRα.

GM-CSFRα/IL-3Rα chimera: this fusion cDNA is the converse of the IL-3Rα/GM-CSFRα chimera and encodes the first 118 amino acids of GM-CSFRα-chain including the signal sequence fused to amino acids 104–378 of IL-3Rα. It was generated by PCR using a sense primer corresponding to codons 104–110 of IL-3Rα and includes a Kpn 1 site. A downstream antisense primer was also used. The resulting PCR product was sequenced and ligated in-frame to the Kpn 1 site at codon 118 of GM-CSFRα.

IL3Rα (−31) flag: this cDNA encodes an N-terminally truncated form of the IL-3Rα which lacks the first 31 amino acids of the mature protein but includes an 8 amino acid "flag" peptide sequence between the putative signal sequence and residue 50 of IL-3Rα. This cDNA was generated by digesting wild-type IL-3Rα with the restriction endonuclease EcoR V (Boehringer Mannheim GmbH, Germany), which cleaves between codons 49 and 50 and ligating it to a PCR-generated fragment encoding the 18 amino acid signal sequence of the IL-3Rα the "flag" sequence and a short multicloning sequence which results in Val-Asp-Asp separating the flag peptide and IL-3Rα. PCR-generated sequences were verified by DNA sequence analysis.

IL-3Rα flag: this cDNA encodes an IL-3Rα in which the putative signal sequence of IL-3Rα (first 18 amino acids) is fused to the flag peptide. It was generated by PCR using an upstream sense primer corresponding to codons 19–26 and carrying an Xba I site at the 5' terminus of the primer. The downstream antisense primer corresponded to codons 104–99. The resultant PCR product was ligated at the 3' end to IL-3Rα (−31) flag using a common BamH 1 site to restore the coding sequence for the N-terminal 31 amino acids missing from IL-3Rα (−31) flag. The 5' end of the PCR product was ligated via the Xba I site to the 3' end of a PCR generated fragment encoding the IL-3Rα signal peptide followed by the "flag" sequence plus the extra amino acids Val-Asp-Asp-Ile-Ser-Arg. The fidelity of the PCR generated portion was verified by DNA sequence analysis.

All chimera and truncation constructs were cloned into the expression PMX139 prior to transfection into COS cells by DEAE-dextran. Cells were grown to approximately 50–70% confluence, washed free of medium and then incubated with 3 μg of cDNA (per 10 cm plate) or 6 μg of cDNA (per 15 cm plate) with 0.25 mg/ml DEAE-dextran. After approximately 30 min the DEAE-dextran solution was aspirated off and cells washed and incubated in IMDM supplemented with 10% FCS and 100 μM chloroquine for 3–5 hours. Finally the cells were washed 3 times with serum free medium and incubated with IMDM supplemented with 10% FCS for 40–60 hours at 37° C.

RESULTS

Figure 1A:
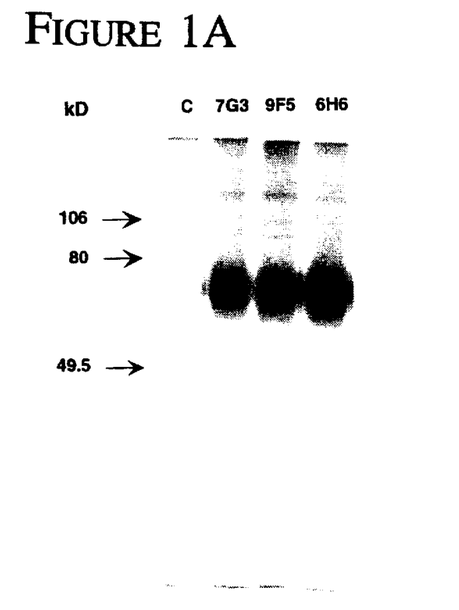
FIG. 1A Is a depiction of an Immuno-precipitation of IL-3Rα chain from $^{125}$I surface-labelled F6 cells, FIG. 1B Is a depiction as for FIG. 1A except showing a Western blot of F6 cells. The analyses of both FIG. 1A and FIG. 1B were performed on 10% SDS-PAGE under reducing conditions. The MW markers are indicated by arrows on the left-hand side of each gel.
Figure 1B:
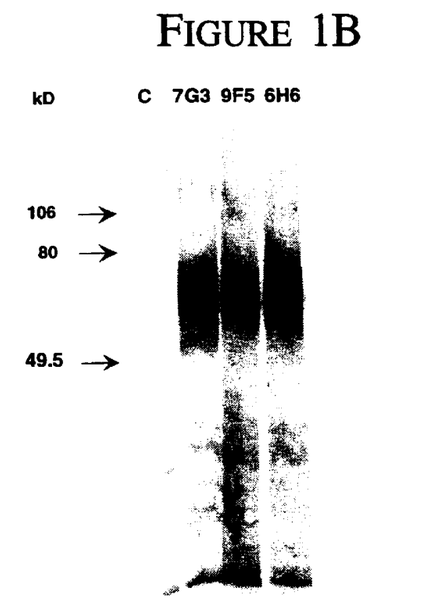
Figure 1C:
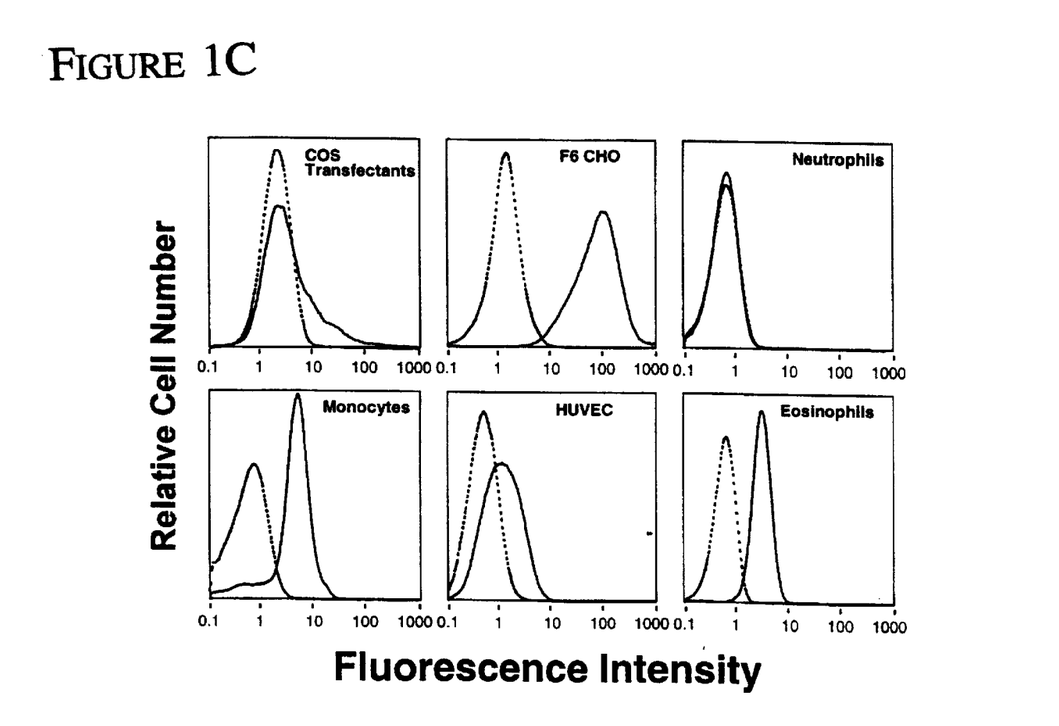
FIG. 1C Is a flow cytometry analysis of stainings of MoAb 7G3 (−) and the control MoAb (- - -) to COS cells transiently transfected with IL-3R α-chain, F6 cells, neutrophils, monocytes, HUVEC and eosinophils, for the experiments shown in FIGS. 1A and 1B.

Development of MoAb 7G3. MoAb 7G3 and other anti-IL-3Rα MoAb 6H6 and 9F5 were raised by immunizing mice with COS cell transfectants expressing the IL-3Rα chain on their surface and selecting on the stable CHO cell transfectant F6 which expresses 4×10$^5$ IL-3R α chains per cell. MoAb 7G3 as well as MoAb 6H6 and 9F5 bound strongly to F6 cells (FIG. 1C) but not to untransfected CHO cells or CHO cell transfectants expressing GM-CSFRα chain (data not shown). To confirm biochemically the identity of the antigen identified by MoAb 7G3 as the IL-3Rα chain, immunoprecipitation and Western blot analysis were carried out. MoAb 7G3 as well as MoAb 9F5 and 6H6 specifically immunoprecipitated a protein of MW 70,000 from $^{125}$I surface-labelled F6 cells whereas a control anti-GM-CSFRα chain MoAb failed to do so (FIG. 1A). MoAb 7G3, 9F5 and 6H6 also recognized a protein of MW 70,000 in Western blotting of F6 cells (FIG. 1B). No immunoprecipitated or Western blotted bands were seen when untransfected CHO cells were used (data not shown). Consistent with the known distribution of the IL-3R, MoAb 7G3 stained monocytes, HUVEC and eosinophils but not fresh neutrophils (FIG. 1C), further confirming the identity of the antigen as the IL-3Rα chain. Identical staining was seen with 6H6 and 9F5 (data not shown). MoAb 7G3 is classified as a mouse IgG$_{2a}$, and 6H6 and 9F5 are mouse IgG$_1$.

Figure 2A:
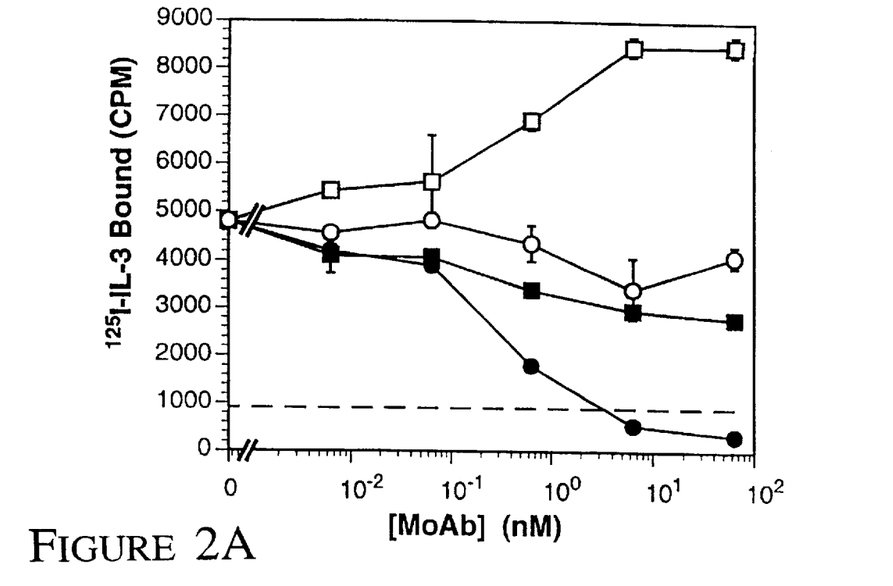
FIG. 2A. Is a graph showing dose-dependent competition for $^{125}$I-IL-3 binding by MoAb 7G3 (●), 6H6 (□), 9F5 (■) and a control MoAb (○) to F6 CHO cells stably expressing the IL-3R α-chain
Figure 2B:
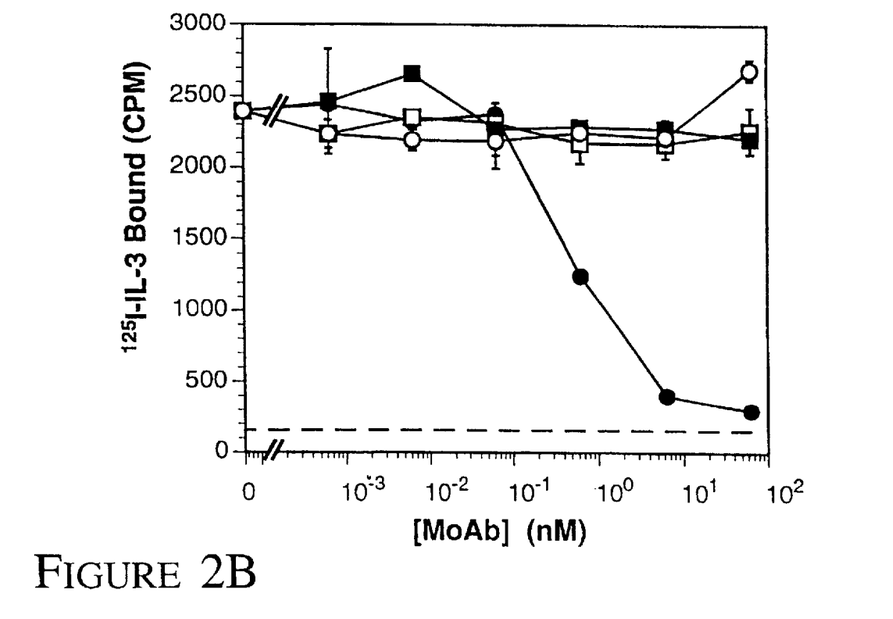
FIG. 2B is a graph as in FIG. 2A except showing binding to COS cells transiently transfected with IL-3R α- and β-chains.
Figure 3A:
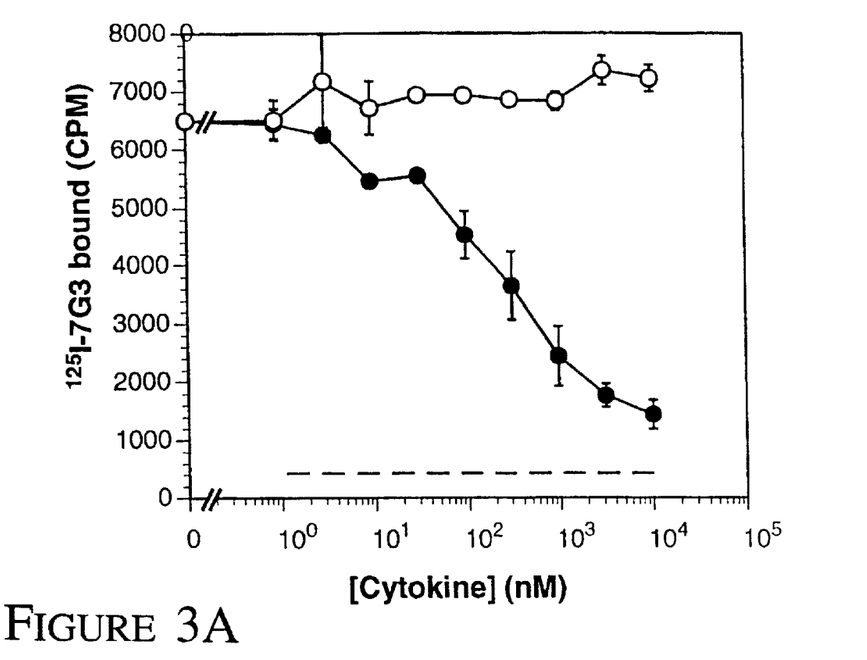
FIG. 3A. Dose-dependent competition for $^{125}$I-7G3 binding to F6 cells stably expressing the IL-3R α chain.
Figure 3B:
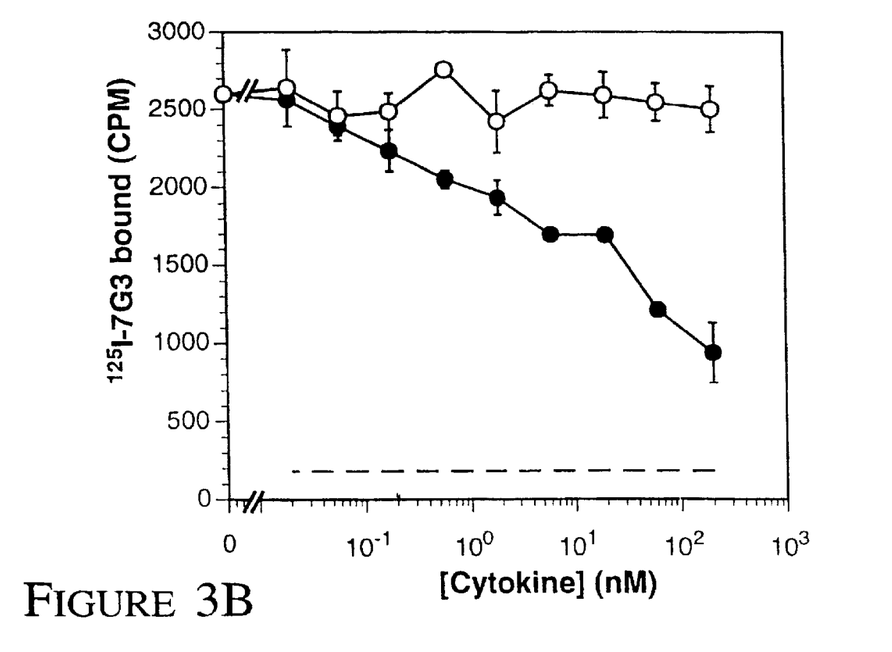
FIG. 3B is a graph as in FIG. 3A except that binding is to COS cells transiently transfected with the IL-3R α and β chains by human IL-3 (●) or GM-CSF (○). In both FIGS. 3A and 3B the dashed line represents the inhibition in the presence of 100 fold excess unlabelled 7G3 and each point represents the mean of triplicate determinations and the error bars represent standard deviations.

Reciprocal inhibition of binding between IL-3 and MoAb 7G3. To examine whether the anti-IL-3Rα chain MoAb could interfere with IL-3 binding we next performed competition experiments using $^{125}$I-IL-3 and cells expressing the low or high affinity IL-3 receptors. We found that MoAb 7G3 but not other MoAb inhibited the binding of $^{125}$I-IL-3 to F6 cells expressing IL-3Rα in a dose-dependent manner (FIG. 2A). Similarly MoAb 7G3 also blocked the binding of $^{125}$I-IL-3 to COS cells transfected with the IL-3Rα and β chain cDNA (FIG. 2B). In both cases, MoAb 7G3 gave 50% inhibition of $^{125}$I-IL-3 binding around 0.7 μM and complete inhibition around 10 μM. MoAb 6H6 and 9F5 did not inhibit IL-3 binding to low or high affinity IL-3 receptors, however, 6H6 enhanced $^{125}$I-IL-3 binding to the IL-3Rα chain above (FIG. 2A) in 3/3 experiments performed. In reciprocal competition experiments F6 cells expressing the IL-3Rα chain alone (FIG. 3A) or COS cells transfected with the IL-3Rα and β chain cDNA (FIG. 3B) were preincubated with IL-3 or GM-CSF over a range of concentration before the addition of $^{125}$I-7G3. In both cases, IL-3 but not GM-CSF inhibited the binding of $^{125}$I-7G3 to the IL-3R.

Figure 4B:
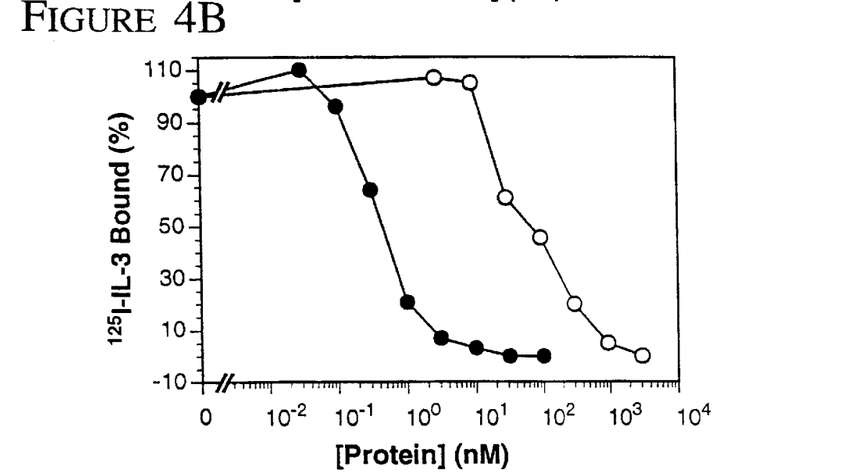
FIG. 4B is a plot showing competition for $^{125}$I-IL-3 binding to F6 cells expressing IL-3Rα chain by MoAb 7G3 (●) or IL-3 (○)
Figure 4C:
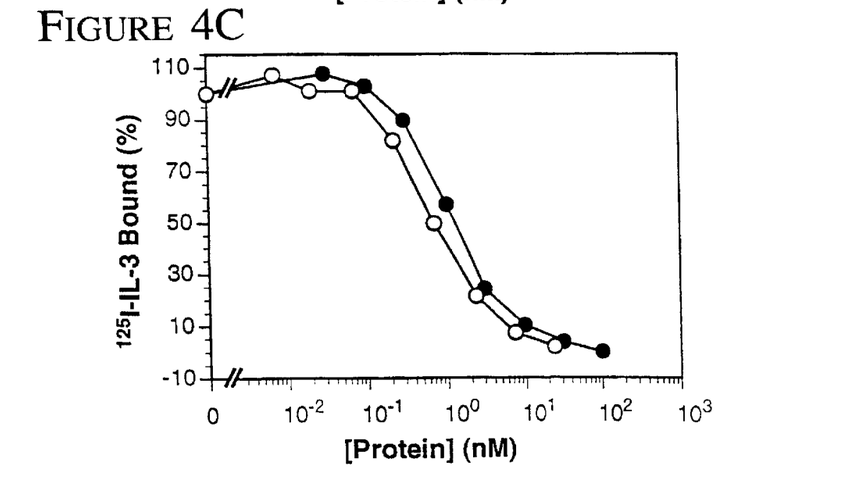
FIG. 4C is a plot showing competition for $^{125}$I-IL-3 binding to COS cells expressing IL-3Rα and β chains by MoAb 7G3 (●) or IL-3 (○). For FIGS. 4A, 4B and 4C each point is the mean of triplicate determinations.

The affinity of MoAb 7G3 for the IL-3Rα chain Having established that MoAb 7G3 and IL-3 recognized the same or adjacent binding sites on IL-3Rα chain we next performed direct measurements of MoAb 7G3 binding and compared them to IL-3 binding. Scatchard transformation of a saturation binding curve of $^{125}$I-7G3 on F6 cells revealed a K$_D$ of 900 pM (FIG. 4A). This represents a hundred fold higher affinity of IL-3Rα for 7G3 than reported for IL-3 itself.[16] Consistent with these values MoAb 7G3 competed with an approximately 100 fold greater affinity than IL-3 for $^{125}$I-IL-3 binding to F6 cells (FIG. 4B). On the other hand, MoAb 7G3 competed with approximately three fold lower affinity than IL-3 on COS cells expressing the IL-3 high affinity receptor (FIG. 4C).

MoAb 7G3 antagonizes IL-3-mediated biological functions. Since IL-3 is a pleiotropic cytokine capable of stimulating multiple cell types and functions, we examined whether MoAb 7G3 could antagonize IL-3 functions in situations where IL-3 may play a pathogenic role, namely stimulation of cell proliferation, basophil histamine release and endothelial cell activation. To study effects on proliferation, we used the TF-1 cell line which is dependent on IL-3 for growth. A dose-response study indicated that a concentration of approximately 0.3 ng/ml of IL-3 stimulated half-maximal proliferation of TF-1 cells (FIG. 5A). We found that the addition of MoAb 7G3, but not other anti-IL-3Rα chain MoAbs, to TF-1 cells stimulated with 0.3 ng/ml IL-3 antagonized cell proliferation in a dose-dependent manner (FIG. 5B).

IL-3 has been shown to be one of the strongest enhancer of histamine release from human basophils, suggesting an effector role in allergy.[4,14] From a dose-response of IL-3 (FIG. 6A) we selected a concentration of 1 ng/ml to examine the effect of MoAb 7G3. We found that MoAb 7G3, but not MoAb 9F5, was able to completely antagonize the IL-3-dependent stimulation of basophil histamine release (FIG. 6B).

Human endothelial cells have recently been shown to express IL-3 receptor α and β chain[7,34] and it has been demonstrated that IL-3 acts as an amplification factor enhancing several endothelial cell functions including cytokine secretion.[8] We found that MoAb 7G3 was able to antagonize the synergy of IL-3 with interferon γ in the stimulation of IL-6 secretion. This effect was specific for the IL-3 amplification effect and did not affect the small stimulatory effect of interferon γ alone (FIG. 7A). Similarly, MoAb 7G3 was able to antagonize the enhancing effect of IL-3 on IL-8 secretion by TNF-α-stimulated cells without inhibiting the effect of TNF-α (FIG. 7B).

Epitope mapping of MoAb 7G3. To identify the region(s) in IL-3Rα recognized by MoAb 7G3 we initially tested MoAb 7G3 for binding to overlapping peptides of 14 amino acids in length encompassing the full extracellular domain of the IL-3Rα chain. However, no specific binding of MoAb 7G3 was observed (data not shown). Since these results suggest that MoAb 7G3 may recognize a conformational rather than a linear epitope we generated cDNAs encoding IL-3Rα/GM-CSFRα chimeras and truncated IL-3Rα chains (FIG. 8A). These cDNAs were expressed in COS cells and binding of MoAb 7G3 to the mutant receptors was examined by Western blotting and immunofluorescence. Although the IL-3Rα/GM-CSFRα chimera composed of amino acids 1–104 of IL-3Rα and amino acids 118–400 of GM-CSFRα bound 7G3 by both Western blot analysis (FIG. 8B) and immunofluorescent microscopy (data not shown), the converse chimera (GM-CSFRα/IL-3Rα) composed of amino acids 1–118 of GM-CSFRα and amino acids 10–378 of IL-3Rα failed to do so. This suggests that the epitope for 7G3 is located in the amino terminal 104 amino acids of IL-3Rα. A receptor deletion mutant, IL-3Rα (–31) flag, lacking the first 31 residues beyond the signal peptide (Thr19-Asp49 absent) but containing an 8 residue "flag" sequence also failed to bind 7G3. However another receptor mutant, IL-3Rα flag, containing Thr 19-Asp 49 along with the "flag" sequence did bind 7G3 (FIG. 8B). Strong expression of the IL-3Rα (–31) flag and IL-3Rα flag could be demonstrated by immunofluorescent microscopy (data not shown) and Western blotting (FIG. 8C) using an anti-flag M2 MoAb. These results suggest that the epitope of 7G3 may be located within amino acids Thr19-Asp49 of the amino terminus of IL-3Rα.

DEPOSIT OF CELL LINE

The cell line 7G3 was deposited on the Dec. 29, 1995 in the American Type Culture Collection 10801 University Boulevard, Manassas, Va. 20110-2209, United States of America and has been designated HB-12009.

REFERENCES

1. Clark and Kamen (1987) *Science* 236:1229,
2. Sieff et al (1987) *J Clin Invest* 80:818,
3. Lopez et al (1988) *Blood* 72: 1797,
4. Haak-Frendscho et al (1988) *J Clin Invest* 82: 17,
5. Elliott et al (1989) *Blood* 74: 2349,
6. Saeland et al (1993) *J Exp Med* 178: 113,
7. Korpelainen et al (1993) *Proc Natl Acad Sci USA* 90:11137,
8. Korpelainen et al (1995) *Blood* 86:176–182
9. Orazi et al (1992) *Blood* 79: 2610,
10. Deliwel et al (1988) *Blood* 72:1944,
11. Park et al (1989) *Blood* 74:56,
12. Clayberger et al (1992) *J Exp Med* 175:371,
13. Valent et al (1989) *Blood* 73: 1763,
14. Lopez et al (1990) *J Cell Physiol* 145:69,
15. Kay et al (1991) *J Exp Med* 173:775,
16. Kitamura et al (1991) *Cell* 66: 1165,
17. Hayashida et al (1990) *Proc Natl Acad Sci USA* 87:9655,
18. Kitamura and Miyajima (1992) *Blood* 80:84,
19. Ihleet al (1994) *Trends Biochem Sci* 19: 222,
20. Bazan (1990) *Proc Natl Acad Sci USA* 87: 6934,
21. Goodall et al (1993) *Growth Factors* 8: 87,
22. Hercus et al (1994) *Blood* 83:3500,
23. Woodcock et al (1994) *EMBO J* 13: 5176,
24. Banry et al (1994) *J Biol Chem* 269: 8488,
25. Galfre et al (1977) *Nature* 266: 550,
26. Rathjen and Geczy (1986) *Hybridoma* 5: 255,
27. Lyons (1985) *J Immunoassay* 6: 325,
28. Krissansen et al (1989) *International Immunol* 2:267,
29. Lopez et al (1989) *Proc Natl Acad Sci USA* 86: 7022,
30. McConahey and Dixon: (1980) *Methods Enzymol* 70(A): 210
31. Scatchard (1949) *Ann NY Acad Sci* 51:660,
32. Shaff and Beavan (1979) *Analyt Biochem* 94:425
33. Gamble et al (1989) *Proc Natl Acad Sci USA* 36:7169
34. Brizzi et al (1993) *J Clin Invest* 91:2887
35. Sato et al (1993) *Blood* 82:752
36. Lopez et al (1989) *Proc Natl Acad Sci USA* 86:7022
37. Metcalf: The hemopoietic colony stimulating factors, Elsevier, Amsterdam, (1984), p493
38. Metcalf (1991) *Science* 254:529
39. Metcalf et al (1986) *Blood* 68: 46
40. Falk et al (1991) *Am J Clin Pathol* 95:355
41. Ryan et al (1994) *Mol Reprod Develop* 39:200
42. Smith et al: (1995) *Blood* 86, 3938–3944
43. Stomski et al (1996) *Mol. Cell Biol* 16:3035

What is claimed is:

1. A method of treating a patient suffering from a condition resulting from an overproduction of IL-3, said method comprising the step of administering to said patient a monoclonal antibody or antibody fragment thereof with a binding specificity for amino acid residues 19–49 of said IL-3 receptor α-chain in an effective amount to antagonize functions of said IL-3.

2. The method according to claim 1 wherein said monoclonal antibody is produced by the 7G3 hybridoma cell line having an ATCC accession number HB-12009.

3. The method according to claim 2, wherein said antibody fragment is selected from the group consisting of an Fab fragment, and an Fv fragment.

4. The method according to claim 3, wherein said antibody fragment is recombinant.

5. The method according to claim 1 wherein said condition is selected from the group consisting of myeloid leukaemias, lymphomas and allergies.

6. A pharmaceutical preparation comprising a monoclonal antibody or fragment thereof with a binding specificity for amino acid residues 19–49 of the IL-3 receptor α-chain in combination with a physiologically acceptable carrier, said antibody or antibody fragment being included in said preparation in an amount effective to antagonize functions of IL-3 to treat a condition resulting from overexpression of IL-3.

7. The preparation according to claim 6, wherein said monoclonal antibody is produced by the 7G3 hybridoma cell line having an ATCC accession number HB-12009.

8. The method according to claim 7, wherein said antibody fragment is selected from the group consisting of an Fab fragment, and an Fv fragment.

9. The preparation according to claim 8, wherein said antibody fragment is recombinant.

10. The preparation according to claim 6 wherein said condition is selected from the group consisting of myeloid leukaemias, lymphomas and allergies.

* * * * *